United States Patent
Saadat et al.

[11] Patent Number: 6,056,747
[45] Date of Patent: May 2, 2000

[54] APPARATUS AND METHOD FOR TREATMENT OF BODY TISSUES

[75] Inventors: Vahid Saadat, Redwood Shores; Malcolm M. Farnsworth, Menlo Park, both of Calif.

[73] Assignee: Gynecare, Inc., Menlo Park, Calif.

[21] Appl. No.: 08/905,189

[22] Filed: Aug. 4, 1997

[51] Int. Cl.$^7$ .................................................. A61B 17/39
[52] U.S. Cl. ................................ 606/50; 606/42; 606/45; 607/101
[58] Field of Search .................................. 606/41, 45–50, 606/42; 607/98–101

[56] References Cited

U.S. PATENT DOCUMENTS 4,682,596   7/1987   Bales et al. .

FOREIGN PATENT DOCUMENTS

| 94 07413 | 4/1994 | WIPO . |
| 96 00042 | 4/1996 | WIPO . |
| 96 36860 | 11/1996 | WIPO . |
| 97 15238 | 5/1997 | WIPO . |
| 97 00646 | 9/1997 | WIPO . |

*Primary Examiner*—Linda C. M. Dvorak
*Assistant Examiner*—Roy Gibson
*Attorney, Agent, or Firm*—Verne E. Kreger

[57] ABSTRACT

An apparatus, system, and method for treating body tissue includes an electrode assembly having a first electrode and a second electrode, with at least the first electrode formed of a foam-like material. Conductive fluid is delivered to the operating site, which may involve injecting the conductive fluid through the porous foam-like material of the first electrode via a fluid supply conduit. The apparatus may also include a fluid withdrawal conduit. The second electrode may also be formed of a foam-like material. The electrode assembly may be positioned on a catheter shaft having a distal end, with the first electrode positioned on the catheter shaft distal end. In treating desired tissue at a selected operational site, the electrode assembly is introduced to the site with one or more of the first electrodes positioned adjacent to the desired tissue. Conductive fluid, such as a saline solution, is delivered to the operational site via the supply conduit. Electrical power is provided across the first electrode and second electrode via a power supply, which may be an RF power supply.

20 Claims, 7 Drawing Sheets

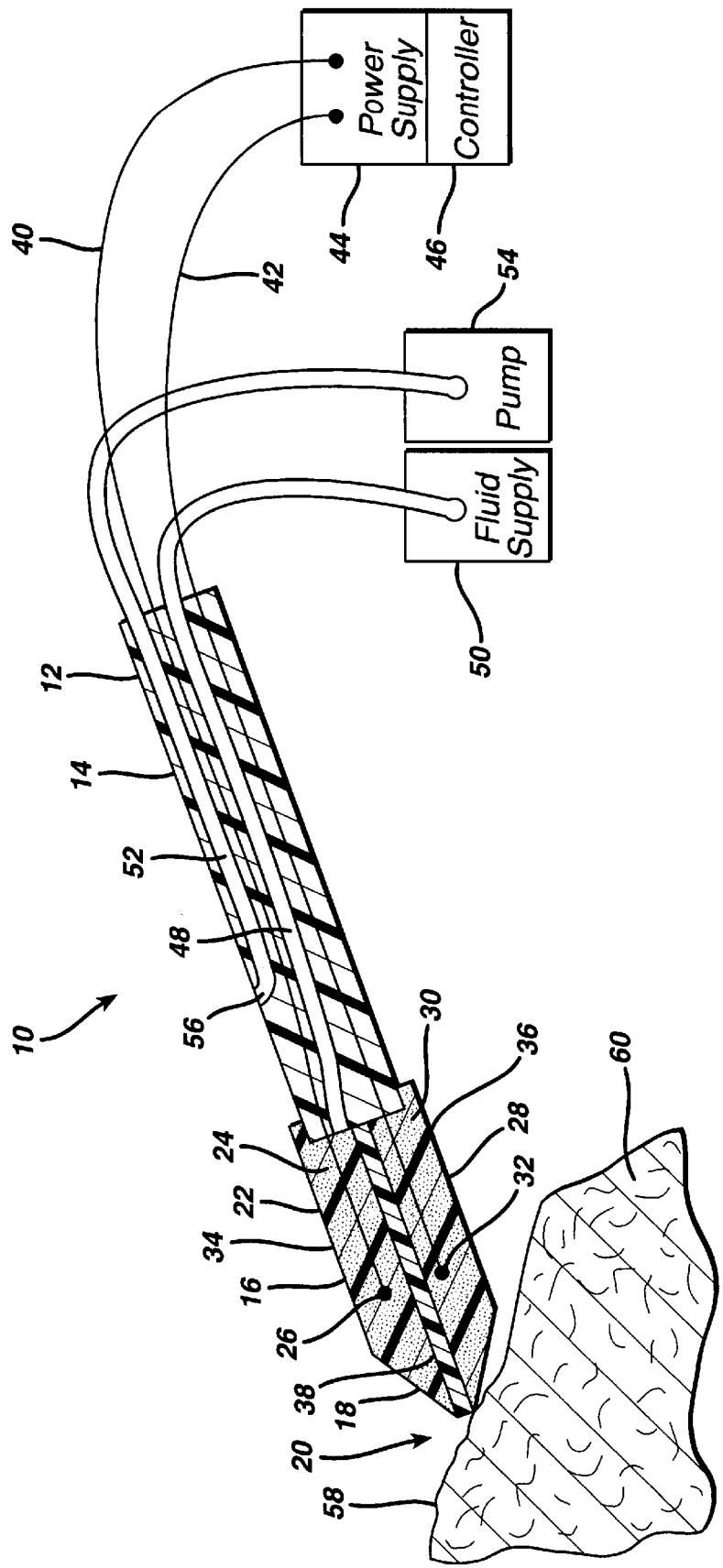

APPARATUS AND METHOD FOR TREATMENT OF BODY TISSUES

BACKGROUND OF THE INVENTION

1. Field of the Invention

The invention relates to a device for treatment of body tissues. More particularly, the present invention relates to an apparatus and method for treatment, including vaporization and coagulation, of body tissues using an electrode comprising a porous, foam-like material in conjunction with a conductive fluid such as saline.

2. Description of Related Art

Electrosurgery has been used for treating body tissue, including coagulation, desiccation, and vaporization of tissue. A common method of performing electrosurgery involves injecting conductive fluid, such as saline solution, into the operational site. The conductive fluid serves to create an electrical path between the electrodes and the body tissue.

Continuous replenishment of the conductive fluid can be important during various procedures. The fluid can be absorbed by the patient's body. Furthermore, fluid may become contaminated, thus compromising its conductivity and/or other desirable characteristics, such as clarity.

When sufficient power is applied to an active electrode in the presence of a conductive fluid and body tissue, the electrical current will flow from the active electrode, through the conductive fluid, and into the tissue. The electrical power can cause various tissue effects, including coagulation, necrosis, and desiccation.

Various electrode configuration are known for spot treatments of body tissues. Many prior art electrode assemblies include a stiff metal active electrode, which is generally rigid and non-yielding. A surgeon can push the active electrode of such rigid configurations into the tissue to be treated, thereby reaching tissues that are beneath the natural tissue surface.

For treating a generally uneven tissue surface, a brush electrode is known that is formed from numerous wires, each of which acts as an active electrode. As the brush is drawn across the tissue surface, the individual brush wires generally follow the tissue surface.

In some applications, it may be desirable to treat large surface areas of tissue. For example, in treating endometriosis, it is desirable to coagulate large areas of selected body tissue that may be surrounded by other body tissue. Treatment of endometriosis typically involves coagulating tissue that can be located throughout the abdominal cavity. However, due to the inconsistent tissue surfaces presented during such applications, coagulating the desired tissue can be difficult and time-consuming, particularly where large surface areas are involved. A hard, rigid electrode may not easily conform to the tissue surface, thus missing recessed surface areas. Increasing the power may allow recessed areas to be treated in a single pass, but the surrounding tissue, which the user may not want to treat, may be inadvertently impacted by the higher power.

Consequently, there is a need to efficiently coagulate desired body tissue while minimizing harm to surrounding tissue. The present invention satisfies these needs.

SUMMARY OF THE INVENTION

Briefly and in general terms, the present invention provides an electrosurgical instrument and system for treating tissue at a selected operation site, including a first electrode comprising foam-like material, such as polyurethane foam, silicone foam, or porous ceramic, and a first electrical lead in electrical connection with the first electrode. The instrument may further include a fluid supply conduit in fluid communication with the foam-like material of the first electrode, wherein fluid may be supplied to the operation site via the foam-like material and fluid supply conduit. A fluid withdrawal conduit may be used to withdraw fluid from the operational site.

The instrument may include a second electrode comprising foam-like material. The second electrode may be positioned in adjacent to the first electrode. An insulating layer may lie between the first and second electrodes.

The first electrode may be positioned on the shaft distal end, with the second electrode positioned proximal of the first electrode. The fluid supply conduit may be in fluid communication with the foam-like material of the second electrode, wherein fluid may be supplied to the operation site via the foam-like material of the second electrode.

The invention includes a method of operation that includes providing an electrosurgical instrument having an electrode assembly including a first electrode that includes foam-like material, introducing the electrode assembly into a selected operation site, placing the first electrode adjacent the selected tissue, surrounding the electrode assembly with a conductive fluid so that the conductive fluid defines an electrical path between the first electrode and the selected tissue, and applying sufficient output power to the electrode assembly to induce a desired treatment on the selected tissue. In a further embodiment, the electrosurgical instrument includes a fluid delivery conduit in fluid communication with the foam-like material of the first electrode, and the method of use includes delivering conductive fluid through the fluid delivery conduit to the foam-like material of the first electrode.

In use, the electrode assembly may be moved across the surface of the tissue, which may include moving the electrode assembly in a back-and-forth motion. The electrode assembly may also be used in a dabbing motion.

Other features and advantages of the present invention will become more apparent from the following detailed description of the invention when taken in conjunction with the accompanying drawings.

BRIEF DESCRIPTION OF THE DRAWINGS

FIG. 1 is a side view, in partial cross section, of a system according to one embodiment of the present invention.

DETAILED DESCRIPTION OF THE PREFERRED EMBODIMENTS

Figure 1A:
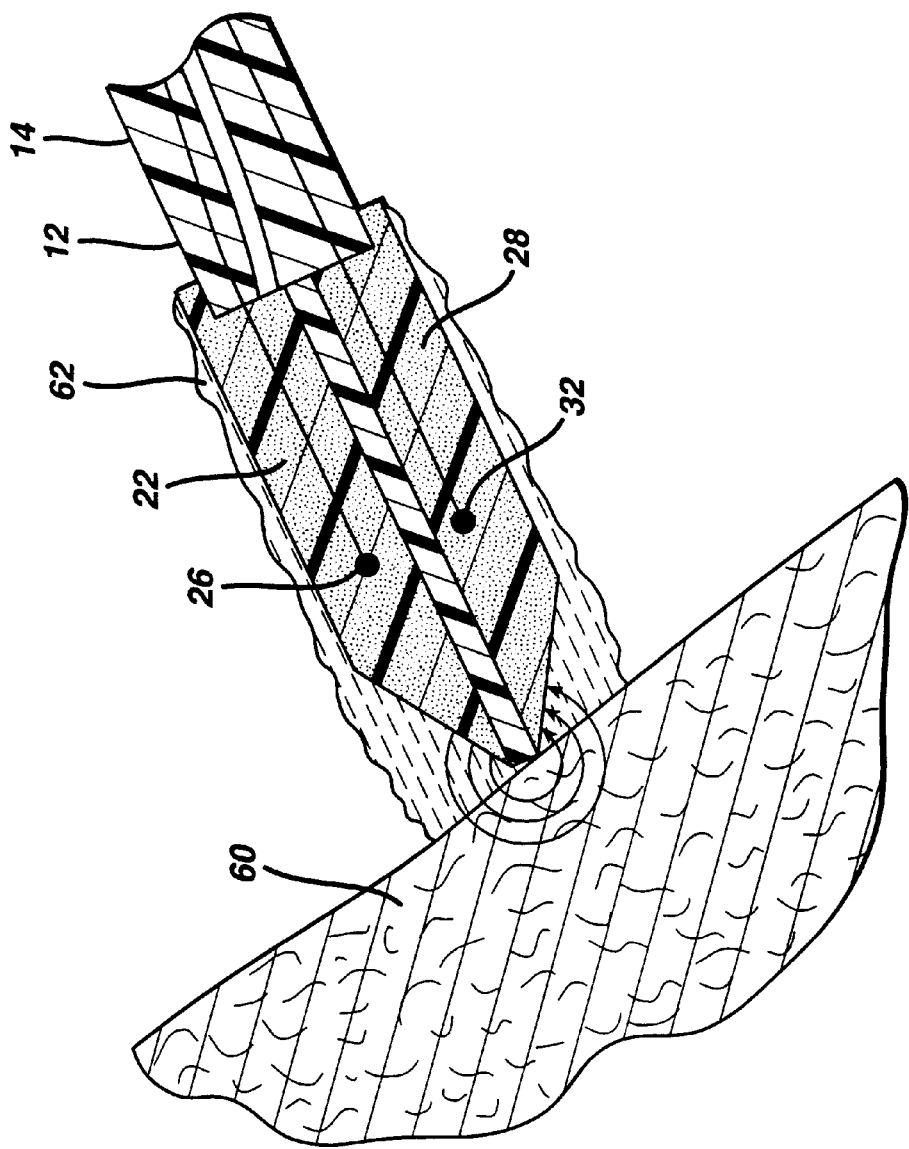
FIG. 1a is a close-up side view, in cross section, of the electrosurgical instrument depicted in FIG. 1.

The present invention is depicted in FIGS. 1 through 6 for use in treating body tissues, including use in treating tissue within a human abdominal cavity and a human uterus. However, the present invention is not limited to such uses, and may be applied to various electrosurgical procedures.

Referring now to FIG. 1, in one preferred embodiment the system 10 of the invention comprises an electrosurgical instrument 12 including a generally elongated shaft 14 having an electrode assembly 16 at the shaft distal end 18. The electrode assembly 16 is shown positioned at a desired operational site 20. The electrode assembly 16 includes a first electrode 22, which includes a foam portion 24 formed of a foam-like material. Polyurethane foams, polymeric-type foams, silicone foams, porous ceramic, and other porous foam-like materials may be used. The foam-like material may be flexible to allow the foam portion 24 to conform to uneven surfaces, as depicted in FIG. 2, or it may be substantially rigid.

In the embodiment shown, the first electrode 22 also includes a conductive portion 26, such as a metal strip, which is in electrical contact with the foam portion 24. When the foam portion is soaked with a conductive fluid, the conductive fluid is in electrical contact with the conductive portion 26.

The electrode assembly 16 may include a second electrode 28 positioned on the shaft 14. The second electrode 28 itself comprises, in the embodiment shown, a foam portion 30 and a conductive portion 32. When the foam portion is soaked with an electrically conductive fluid, the electrically conductive fluid is in electrical contact with the conductive portion 32.

The first electrode 22 and second electrode 28 are preferably insulated from each other. For example, in the embodiment of FIG. 1, the electrode assembly 16 is generally flat with a first surface 34 and a second surface 36. The first electrode foam portion 22 forms the first surface 34, while the second electrode foam portion 30 forms the second surface 36. In between and separating the first electrode 22 and second electrode 28 is an insulating layer 38 formed of a generally non-conductive material. The insulating layer 38 may be generally water-proof or water-resistant to prevent the conductive fluid from forming a conductive path through the insulating layer 38.

The first electrode 22 and second electrode 28 are electrically connected, via a first electrical lead 40 and a second electrical lead 42, respectively, to a power supply 44 that generates a voltage between the first electrode 22 and second electrode 28. The power supply 44 may be an RF power supply. In the embodiment shown, a controller 46 monitors and controls the output power according to preprogrammed instructions and/or input from the surgeon or other user.

In the embodiment of FIG. 1, a fluid supply conduit 48 within the catheter shaft leads to the first electrode 22, so that fluid introduced to the fluid supply conduit 48 from a fluid supply 50 will flow through and out of the foam portion 24 of the first electrode 22, thereby introducing conductive fluid to the operational site 20.

The fluid supply conduit 48 is shown delivering the conductive fluid into the foam portion of the first electrode 22. However, the fluid may be supplied to various other places and through other means. For example, the fluid may be supplied to the operational site 20 through the second electrode 28 (as an alternative to or in addition to providing the fluid through the first electrode 22). The fluid may also be introduced to the operational site 20 through a fluid port remote from both the first and second electrodes.

A fluid withdrawal conduit 52 may be provided through which fluid may be withdrawn from the operational site 20 by a fluid withdrawal device, such as the fluid withdrawal pump 54 shown in FIG. 1. The fluid withdrawal conduit 52 is shown in FIG. 1 with an intake opening 56 positioned on the catheter shaft 14 proximally of the first electrode 22. Other positions for one or more fluid withdrawal conduits 52 are also within the scope of the invention, including positioning the intake opening 56 within the foam portion 24 of the first electrode 22 and/or the foam portion 30 of the second electrode 28. The withdrawal conduit 52 may even form an assembly which is entirely separate from the main catheter shaft 14. Such a separate assembly, which may comprise a separate catheter shaft, could be independently introduced to and maneuvered around the operational site 20.

Figure 2:
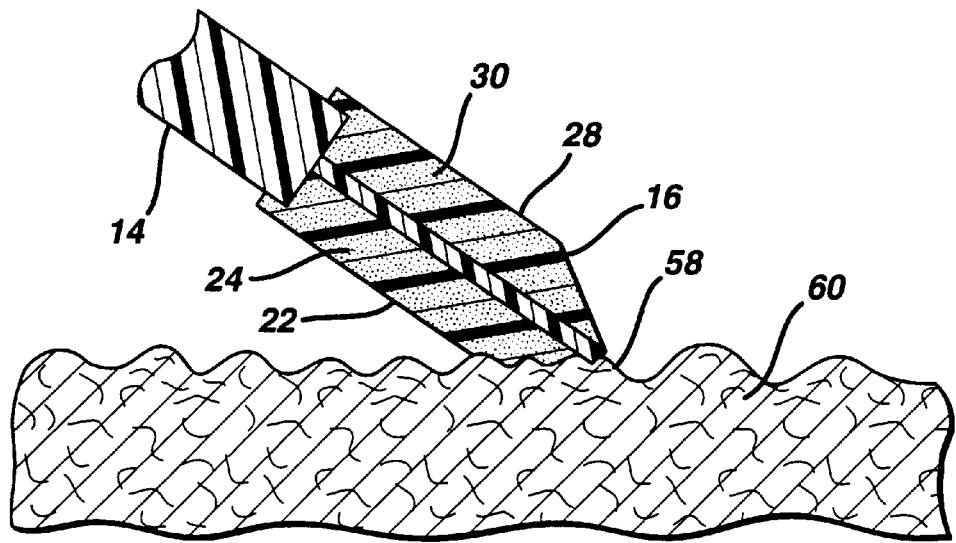
FIG. 2 is a side view, in cross section, depicting the electrosurgical instrument of FIG. 1 in use to treat tissue.

FIG. 1a depicts the electrode 22 positioned adjacent the tissue surface 58. As power is applied between the first electrode 22 and second electrode 28, the current passes from the first electrode 22, through the conductive fluid 62, into the tissue 60, and then to the second electrode 28 via the conductive fluid 62. As the power is thus applied to the tissue 60, the desired treatment to the tissue occurs. As was set forth previously, the desired treatment may include coagulation, desiccation, and/or necrosis of the tissue.

Referring again to FIG. 1, the controller 46 monitors and controls the power supply 44 and hence the power applied across the first electrode 22 and second electrode 28. The controller may also monitor and control the fluid supply 50 and/or the withdrawal pump 54. In the event of a malfunction of either the fluid supply 50, the withdrawal pump 54, or the power supply 44, the controller may operate to shut down operation. For example, the controller 46 may automatically shut off the power supply 44 if the fluid supply 50 is no longer providing fluid to the operational site 20.

Figure 1B:
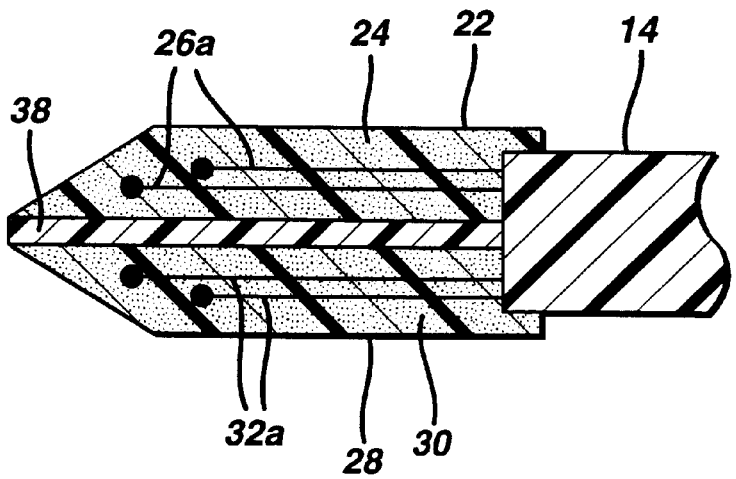
FIG. 1b is a side view, in cross section, of an electrosurgical instrument according to another embodiment of the present invention.
Figure 1C:
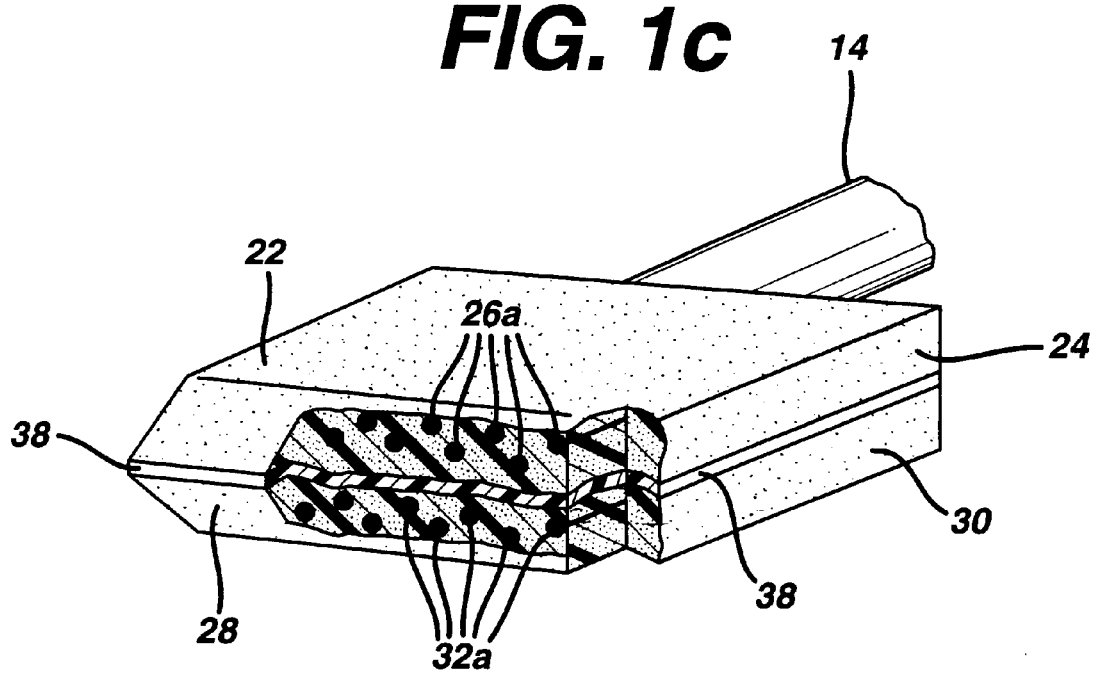
FIG. 1c is a perspective view, in partial cross section, of the electrosurgical instrument of FIG. 1c.

In the embodiment of FIG. 1, the first conductive portion 26 and second conductive portion 32 were single conductors positioned in their respective foam portions 24, 30. As shown in FIGS. 1b and 1c, however, the conductive portions 26a, 32a may each comprise a plurality of small filaments that branch through each foam portion 24, 30. In such an embodiment, electrical power is distributed more evenly across the electrode assembly, which can improve control over the tissue treatment.

FIG. 2 depicts the electrode assembly 16 being drawn across the tissue surface 58, such that the foam portion 24 of the first electrode 22 engages the tissue surface 58. Due to the soft, flexible nature of the foam portion 24 of this particular embodiment, physical trauma caused by moving the electrode assembly 16 across the tissue surface 58 is minimized. The flexible foam portion 24 conforms to the uneven tissue surface 58, so that recessed areas of tissue can be effectively treated. In one embodiment, the foam portion 30 of the second electrode 28 is also flexible, so that it will conform to the tissue surface if drawn across the tissue surface 58 in the manner depicted in FIG. 2 for the foam portion 24 of the first electrode 22.

Figure 2A:
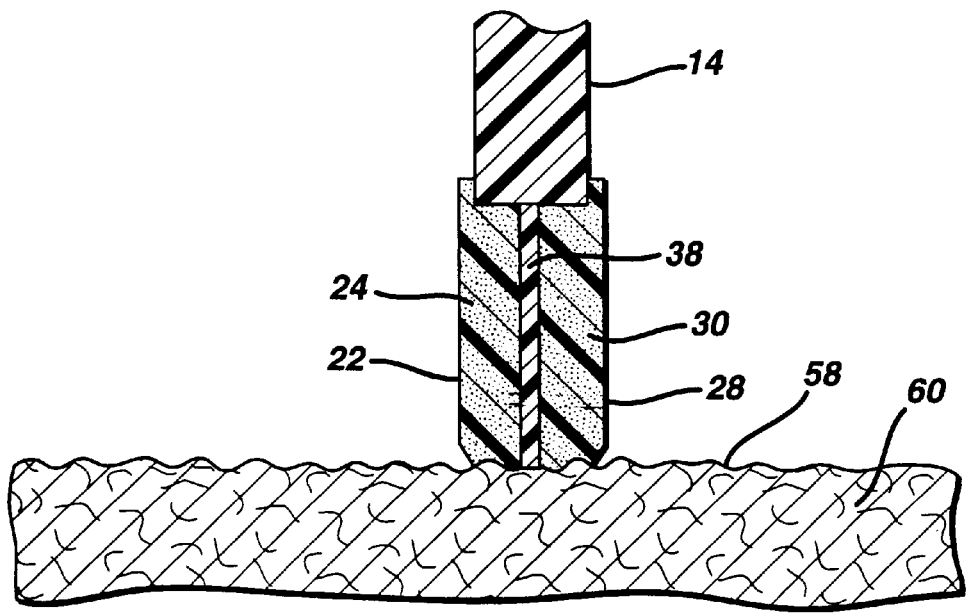
FIG. 2a is a side view, in cross section, depicting the electrosurgical instrument of FIG. 1 in use to treat tissue.

As depicted in FIG. 2a, the insulating layer 38 may also be flexible, so that the distal tip of the electrode assembly may be pressed against the tissue surface 58 to thereby simultaneously engage both the first electrode 22 and the second electrode 28 against the tissue surface, while allowing the instrument to conform to the tissue surface.

Figure 3:
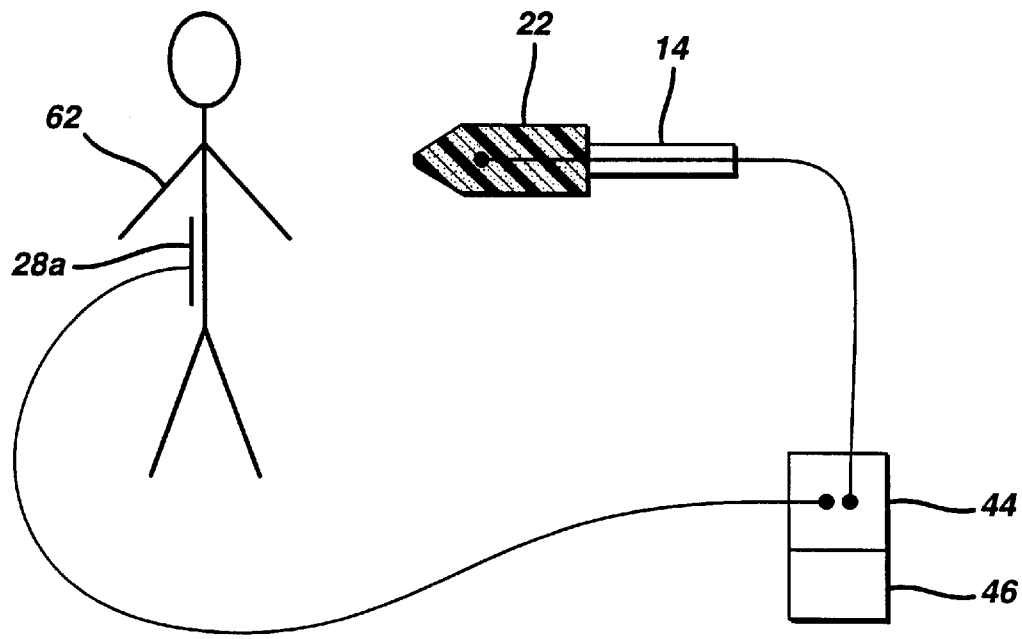
FIG. 3 is a side view, in partial cross section, of an electrosurgical instrument according to an embodiment of the invention.

In the embodiment shown in FIG. 1, the electrode assembly 16 is a bipolar electrode assembly, including a first electrode 22 and a second electrode 28. The invention, however, is also applicable to monopolar electrode assemblies, as shown in FIG. 3. In FIG. 3, the second electrode 28a is a grounding pad which may be positioned in electrical contact with the patient's body 62. In such an embodiment, the patient's body 62 serves as the electrical connection between the first electrode 22 and the second electrode 28a.

Figure 4:
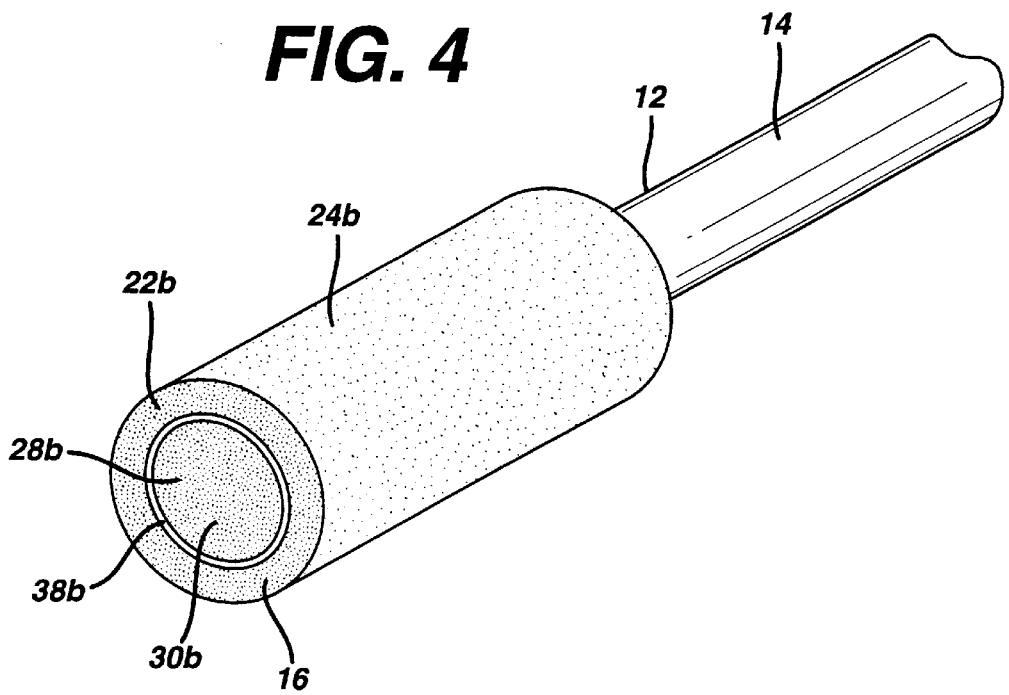
FIG. 4 is a perspective view of an electrosurgical instrument according to an embodiment of the invention.
Figure 4A:
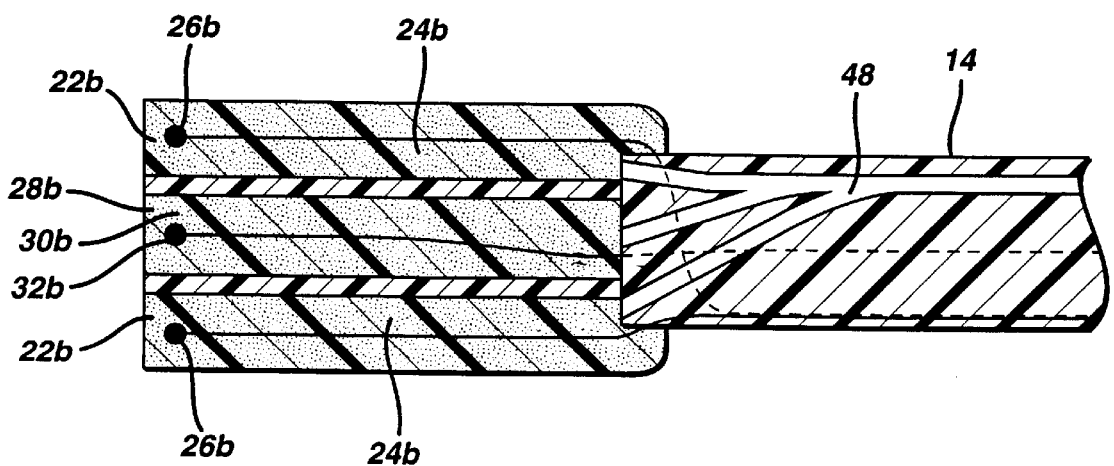
FIG. 4a is close up side view, in cross section, showing details of the electrosurgical instrument of FIG. 4.

Referring now to FIGS. 4 and 4a, in an alternative embodiment of the invention the first electrode 22b is generally cylindrical in shape, and surrounds the second electrode 28b. The first electrode 22b comprises a generally tubular foam portion 24b with one or more conductive portions 26b, such as conductive metal leads. The second electrode 28b comprises a generally cylindrical foam portion 30b, with one or more conductive portions 32b, with the second electrode 28b positioned within the first electrode 22b. A fluid supply conduit 48 within the catheter shaft leads to the first electrode 22b and second electrode 28b.

In the embodiments depicted in FIGS. 1, 1a, and 4a, the conductive leads 26, 32 are depicted as positioned well forward in the foam portions. Such positioning may reduce the resistance between the conductive leads and the patient's tissue, thereby serving to enhance the delivery of power to the patient's tissue.

The conductive leads 26, 32 are depicted in FIGS. 1–4 as being inside the foam material. Such positioning may serve to distribute power more evenly across the tissue surface by dissipating the power through the conductive fluid in the foam portions. The leads may, however, be positioned on the surface of the foam material, either as an alternative to or in addition to positioning such leads within the foam.

Figure 5:
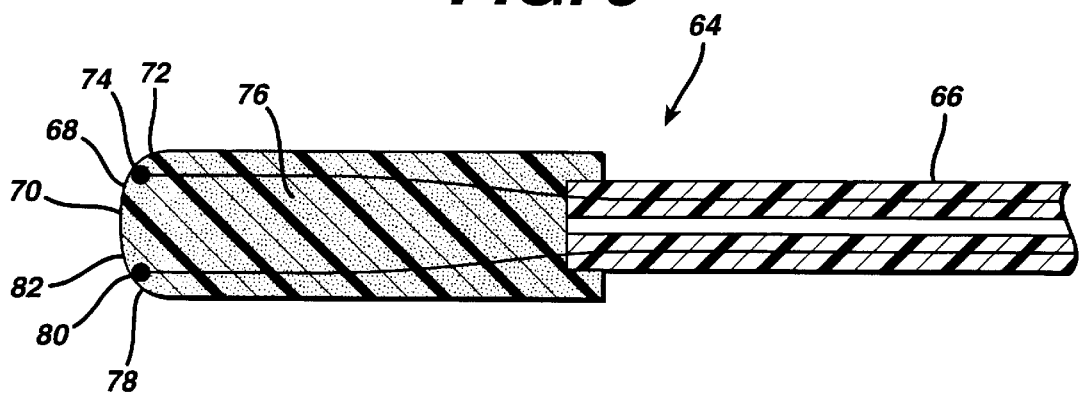
FIG. 5 is a side view, in cross section, of an electrosurgical instrument according to a further embodiment of the invention.

Referring now to FIG. 5, in an alternative embodiment of the invention an electrosurgical instrument 64 includes a catheter shaft 66 with an electrode assembly 68 at the shaft distal end 70, a first electrode 72 comprises a first electrical lead 74 in electrical contact with a main foam portion 76. A second electrode 78 comprises a second electrical lead 80 which is in electrical contact with the main foam portion 76. In such an embodiment, there is no dedicated insulation barrier between the electrodes, as was the case in the embodiments of FIGS. 1–4.

To increase the likelihood that the current will flow from the first electrical lead 74 and into the desired tissue prior to returning to the second electrical lead 80, as opposed to passing directly between the electrical leads 74, 80 via the main foam portion 76, the first and second electrical leads 74, 80 may be positioned at or very near the surface 82 of the central foam portion.

Figure 6:
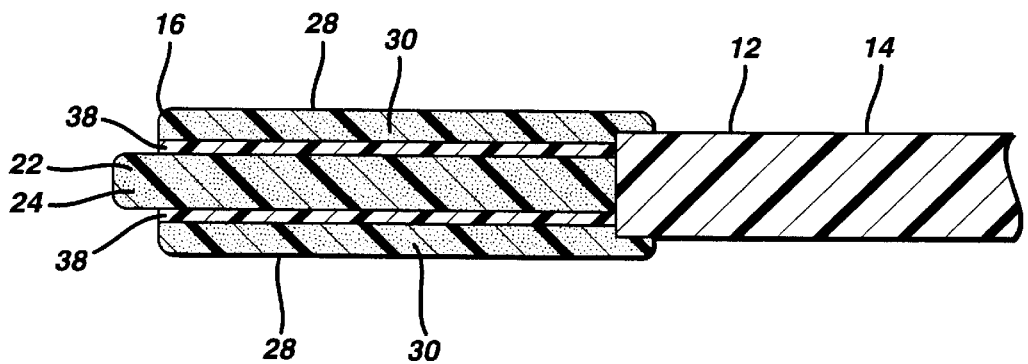
FIG. 6 is a side view, in cross section, of an electrosurgical instrument according to a further embodiment of the invention.

FIG. 6 depicts a further embodiment of the invention, wherein the first electrode 22 is positioned at the distal end of the electrode assembly 16, with the second electrode 28 at a position proximal of the first electrode 22. The insulating layer 38 separates the first and second electrodes 22, 28.

The invention described herein may be used to coagulate tissue, which may involve moving the electrode assembly across the tissue surface in a side-to-side movement, similar to moving a paintbrush across a surface being painted. The instrument may also be used in a "dabbing" manner, where the electrode assembly is pressed against a selected surface area, then lifted and placed against another selected surface area, and so on until all desired areas have been treated.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. An electrosurgical instrument for treating tissue at a selected operation site, the instrument comprising:
   a catheter shaft having a distal end and a proximal end;
   a first electrode comprising a foam-like material and positioned on the shaft distal end, the foam-like material positioned to enable direct contact with the tissue under treatment;
   a first electrical lead in electrical connection with the first electrode;
   a second electrode comprising foam-like material and positioned on the shaft distal end in an opposing relationship to the first electrode;
   a second electrical lead in electrical connection with the second electrode; and
   conductive fluid supply means for providing an electrically conductive path between the first electrode and tissue under treatment.

2. The instrument of claim 1, wherein the conductive fluid supply means comprises a fluid supply conduit in fluid communication with the foam-like material of the first electrode, wherein fluid may be supplied to the operation site via the foam-like material and fluid supply conduit.

3. The instrument of claim 2, further comprising:
   a fluid withdrawal conduit through which fluid may be withdrawn from the operational site.

4. The instrument of claim 2 wherein the fluid supply conduit is in fluid communication with the foam-like material of the second electrode, wherein fluid may be supplied to the operation site via the foam-like material of the second electrode.

5. The instrument of claim 1, wherein the first electrode and second electrode are separated from each other by an insulating layer.

6. The instrument of claim 1, wherein the first electrode further comprises a conductive element passing within the foam-like material of the first electrode.

7. The instrument of 6, wherein the conductive element is positioned in the foam-like material of the first electrode at a position adjacent to a distal end of the instrument.

8. The electrosurgical instrument of claim 1, wherein said second electrode is in a generally surrounding relationship with said first electrode.

9. The electrosurgical instrument of claim 8 wherein said first electrode is positioned on the shaft distal end, and the second electrode is positioned on the shaft proximal of the first electrode.

10. A system for treating tissue at a selected operation site, the system comprising:
   a first electrode comprising a foam-like material the foam-like material positioned to enable direct contact with the tissue under treatment;
   a second electrode electrically insulated from the first electrode;

a first and second lead wire connecting said respective first and second electrodes to a power supply for generating a voltage between the first electrode and the second electrode;

a fluid supply conduit in fluid communication with the foam with the foam-like material of the first electrode;

a fluid source in fluid contact with the fluid supply conduit, wherein fluid may be supplied from the fluid source to the operation site via the foam-like material of the first electrode; and a fluid withdrawal conduit through which fluid may be withdrawn from the operational site.

11. The system of claim 10, further comprising:

a catheter shaft having a distal end and a proximal end, and wherein the first electrode is positioned on the shaft distal end, and the second electrode is positioned on the shaft proximal of the first electrode.

12. The system of claim 10, wherein the power supply comprises an RF power supply.

13. A method of treating selected tissue using an electrode assembly, the method comprising the steps of:

(a) providing an electrosurgical instrument having an electrode assembly including a first electrode and an oppositely disposed second electrode, wherein the first and second electrodes comprise a foam-like material positioned to enable direct contact with the tissue;

(b) introducing the electrode assembly into a selected operation site;

(c) placing the first electrode adjacent the selected tissue;

(d) surrounding the electrode assembly with a conductive fluid so that the conductive fluid defines an electrical path between the first electrode and the selected tissue; and (e) applying sufficient output power to energize the electrode assembly to induce a desired treatment on the selected tissue.

14. The method of claim 13, wherein the electrosurgical instrument further includes a fluid delivery conduit in fluid communication with the foam-like material of the first electrode, and step (d) includes delivering conductive fluid through the fluid delivery conduit to the foam-like material of the first electrode.

15. The method of claim 13, wherein step (c) includes the further step of:

(f) moving the energized electrode across a surface of the tissue.

16. The method of claim 15, wherein step (f) includes moving the energized electrode across the tissue surface in a side-to-side motion.

17. The method of claim 13, wherein step (c) includes the further step of:

(g) dabbing the energized electrode against selected areas of the surface of the tissue.

18. The method of claim 13, wherein the conductive fluid comprises a saline solution.

19. The method of claim 13, wherein the electrode assembly further comprises a second electrode, and step (d) includes surrounding the electrode assembly with a conductive fluid so that the conductive fluid defines an electrical path between the selected tissue and the second electrode.

20. The method of claim 19, wherein the electrosurgical instrument further includes a fluid delivery conduit in fluid communication with the foam-like material of the second electrode, and step (d) includes delivering conductive fluid through the fluid delivery conduit to the foam-like material of the second electrode.

* * * * *